United States Patent [19]
Sato et al.

[11] Patent Number: 5,994,545
[45] Date of Patent: Nov. 30, 1999

[54] PROCESS FOR PRODUCING OPTICALLY ACTIVE AMIDES

[75] Inventors: Takahiro Sato; Kunisuke Izawa, both of Kawasaki, Japan

[73] Assignee: Ajinomoto Co., Inc., Tokyo, Japan

[21] Appl. No.: 09/018,179

[22] Filed: Feb. 3, 1998

Related U.S. Application Data

[62] Division of application No. 08/674,157, Jul. 1, 1996.

[30] Foreign Application Priority Data

Jun. 30, 1995 [JP] Japan .................................. 7-166536

[51] Int. Cl.⁶ ...................... C07D 491/00; C07D 491/12
[52] U.S. Cl. .................................................. 546/92
[58] Field of Search ............................................ 546/92

[56] References Cited

U.S. PATENT DOCUMENTS 5,587,481  12/1996  Allen ........................................ 546/146

OTHER PUBLICATIONS

Chemical Abstracts 136:144124, abstract of Allen, US Patent #5,587,481, 1996.

Chemical Abstracts 114:185380, abstract of Weir, Chem Chron, 18(1), pp. 3–17, 1989.

*Primary Examiner*—D. Margaret M. Mach
*Attorney, Agent, or Firm*—Oblon, Spivak, McClelland, Maier & Neustadt, P.C.

[57] ABSTRACT

The present invention provides a process for producing decahydro(4as, 8aS)isoquinoline-3(S)-carboxamides which are useful as intermediates of Saquinavir (EP 432694). Saquinavir is an anti-AIDS agent. The comprises reacting tetrahydroisoquinoline-3(S)-carboxylic acid with at least one of phosgene, phosgene dimer and triphosgene to form N-carboxy anhydride (NCA), then reacting NCA with an amine to produce a tetrahydroisoquinoline-3(S)-carboxamide derivative, and further reducing this derivative in the presence of a metal catalyst.

1 Claim, No Drawings

PROCESS FOR PRODUCING OPTICALLY ACTIVE AMIDES

This application is a Division of application Ser. No. 08/674,157, filed on Jul. 1, 1996.

BACKGROUND OF THE INVENTION

1. Field of the Invention

The present invention relates to a process for producing decahydro(4aS, 8aS)isoquinoline-3(S)-carboxamides of formula (4) that are useful as an intermediate of Saquinavir (U.S. Pat. No. 5,451,678, also E.P. 432694) which is an anti-AIDS agent owing to the excellent HIV protease inhibition activity.

2. Description of the Background

U.S. Pat. No. 5,256,783 describes a method of producing decahydro(4aS, 8aS) isoquinoline-3(S)-carboxamides, by producing N-tertbutyldecahydro(4aS, 8as)isoquinoline-3(S)-carboxamide in which an amide is introduced into tertbutylamide. The method described in this patent comprises five steps (1) N-protecting L-phenylalanine with benzyl chloroformate, (2) forming a mixed acid anhydride into N-tertbutylamide (84.3%), (3) reacting the resulting amide with formaldehyde in the presence of an acid catalyst to form a tetrahydroisoquinoline compound (66%), (4) N-deprotecting this compound by catalytic reduction using Pd (79%), and (5) obtaining a decahydroisoquinoline compound using an Rh catalyst (59%). However, this method is problematic in that it requires many steps, it has a step with a low yield, Rh is expensive and the reaction has to be strictly controlled to maintain optical purity. Accordingly, the development of a simpler method is desirable.

Further, non-uniform metal catalysts such as Rh, Pt or the like are expensive and are used in nuclear reduction of aromatic rings having functional groups. In contrast, Ru is inexpensive and also causes nuclear reduction of an aromatic ring. However, Ru can only be used in a nuclear reduction of an aromatic ring of a compound free of functional groups, such as toluene or the like. In addition, the influence on the optical activity or the sterically selective reduction is not known.

On the other hand, Chimika Chronika, New Series, 18, 3, 1989 teaches a method of producing tetrahydroisoguinoline-3-carboxamide (the above-mentioned intermediate), wherein tetrahydroisoquinoline-3-carboxylic acid is protected with a benzyloxycarbonyl group (66.5%), the resulting compound is converted into NCA with phosphorus pentachloride (69%), and NCA is reacted with an amine to form an amide (57%). However, since this method is conducted using a racemic compound, it is unclear whether or not optical activity is maintained, the yield in each step is low, and undesirable by-products and industrial waste are formed in large amounts. Accordingly, this method is not industrially useful.

SUMMARY OF THE PRESENT INVENTION

Accordingly, one object of the present invention is to provide a selective, industrially useful process for producing decahydro(4aS,8aS)isoquinoline-3(S)-carboxamides.

The present inventors have assiduously conducted investigations to solve the above-mentioned problems, and have consequently found that tetrahydroisoguinolinecarboxamide can be formed in high yield in two steps: (i) tetrahydroisoquinoline-3(S)-carboxylic acid is reacted with phosgene, phosgene dimer or triphosgene to form tetrahydroisoquinolinecarboxylic acid N-carboxy anhydride (NCA) in high yield without impairing the optical activity, and (ii) reacting NCA with various amines to obtain an amide.

Further, the nuclear reduction of the aromatic ring of tetrahydroisoquinolinecarboxamide has been studied, and it has also been found that the aromatic ring can be nuclearly reduced sterically selectively while maintaining the optical activity with inexpensive Ru rather than expensive metal catalysts such as Rh, Pt and the like, and that the yield given with Ru is higher than that given with Rh.

DETAILED DESCRIPTION OF THE PREFERRED EMBODIMENTS

That is, the present invention relates to a process for producing a tetrahydroisoquinoline-3(S)-carboxamide derivative represented by formula (3), which comprises (i) reacting tetrahydroisoquinoline-3(S)-carboxylic acid of the formula (1)

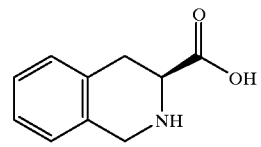

(1)

with at least one of phosgene, phosgene dimer and triphosgene to form N-carboxy anhydride (NCA) of the formula (2),

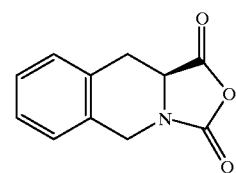

(2)

and (ii) reacting NCA with an amine. The present invention also relates to a process for producing a decahydro(4aS, 8aS)isoquinoline-3(S)-carboxamide derivative of the formula (4)

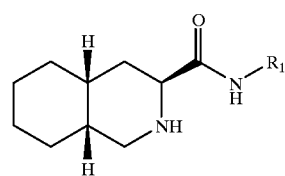

(4)

which comprises the above steps and further comprises reducing a compound of the formula (3)

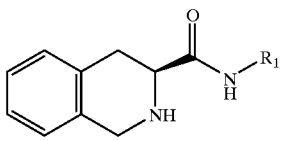

(3)

in the presence of a metal catalyst.

In each of the above formulae, $R_1$ represents hydrogen or a lower alkyl group having from 1 to 6 carbon atoms.

Tetrahydroisoquinolinecarboxylic acid can be obtained by reacting phenylalanine with formaldehyde in the presence of an acid catalyst (Pictet Spengler reaction, Chem. Pharm. Bull., 31, 312, 1983 and Japanese Laid-Open Patent Application (Kokai) No. 157,466/1994). It is industrially mass-produced as an intermediate of Quinapril (see U.S. Pat. No. 4,344,949), an ACE inhibitor.

In the reaction of tetrahydroisoquinoline-3(S)-carboxylic acid (1) with at least one of phosgene, phosgene dimer and triphosgene (hereinafter abbreviated as "phosgene or the like") to form N-carboxy anhydride (2) (hereinafter abbreviated as "NCA"), tetrahydroisoquinoline-3(S)-carboxylic acid is dissolved or suspended in an organic solvent, and phosgene or the like is added to the solution to form NCA. Alternatively, phosgene or the like can be dissolved in the organic solvent and tetrahydroisoquinoline-3(S)-carboxylic acid added to the solution.

Suitable phosgene or the like used in the reaction may be a monomer (phosgene gas), a dimer (phosgene dimer) or a trimer (triphosgene). It is typically used in an amount of from 1 to 10 equivalents, preferably from 1.1 to 1.3 equivalents based on the molar amount of starting material (4).

The organic solvent used is not particularly limited unless it is reacted with phosgene. Suitable solvents include tetrahydrofuran (THF), 1,2-dichloroethane, dichloromethane, toluene and methyl tert-buytl ether. Preferred solvents include THF and dichloromethane because they do not react with the amine in the next reaction, they dissolve tetrahydroisoquinoline-3(S)-carboxamide and NCA, and they have high reactivity.

The reaction is typically conducted at a temperature of from 0 to 100° C., preferably from 40 to 70° C. The reaction time is typically between 0.1 and 36 hours, usually between 2 and 5 hours.

NCA (2) obtained by the reaction can be isolated as a crystal by cooling the reaction solution or charging an inert solvent therein. Examples of suitable inert solvents include hexane, heptane, toluene and dichloromethane.

NCA (2) (tetrahydroisoquinoline-3(S)-carboxylic acid N-carboxy anhydride) represented by the following formula (2)

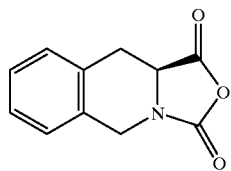

is a novel compound from which the next tetrahydroisoquinoline-3(S)-carboxamide derivative (3) can easily be formed while maintaining the optical activity.

NCA (2) can ordinarily be subjected to the subsequent amidation step as it is. That is, the amidation can be conducted by reacting the above-obtained NCA with ammonia or a lower primary amine having from 1 to 6 carbon atoms. Suitable solvents include THF, 1,2-dichloroethane, dichloromethane, toluene and methyl tert-butyl ether. Preferably, the NCA solution is added to an amine. The solvent used to dissolve NCA is not particularly limited, unless it is reacted with NCA or an amine. THF and dichloromethane are preferable in that these are also used in the preceding reaction.

Suitable amines used in the reaction include ammonia and a lower-alkyl primary amine having from 1 to 6 carbon atoms, preferably a lower-alkyl primary amine having from 1 to 4 carbon atoms. Examples thereof include methylamine, ethylamine, propylamine, isopropylamine, butylamine, isobutylamine, sec-butylamine, tert-butylamine, pentylamine and hexylamine.

In order to form Saquinavir which is the desired compound of the present invention, tert-butylamine is preferable because it can be used as it is. The amine may be dissolved in a solvent or used as a solvent as it is. The amount of the amine is typically between 1 and 50 equivalents, preferably between 2 and 5 equivalents based on the molar amount of NCA.

The reaction proceeds approximately quantitatively at a reaction temperature of from −50 to 70° C., preferably from 0 to 20° C. The reaction time is between 0.01 and 24 hours, usually between 1 and 5 hours.

Compound (3) in which $R_1$ is a tert-butyl group coincides with the product which was separately formed by the process described in U.S. Pat. No. 5,256,783 with respect to all analytical values.

The yield in conversion from phenylalanine to N-tertbutyltetrahydroisoquinolinecarboxamide is 63% when it is calculated on the basis of the yield (81%) in conversion from phenylalanine to tetrahydroisoquinolinecarboxylic acid as described in Japanese Laid-Open Patent Application (Kokai) No. 157,466/1994. Considering the yield of 44% in U.S. Pat. No. 5,256,783, the above-mentioned yield is improved by more than 40%.

The step of (ii) reducing the tetrahydroisoquinoline-3(S) carboxamide derivative (3) into the decahydroisoquinoline-3(S)-carboxamide derivative (4) can be conducted by dissolving tetrahydroisoquinoline-3(S)-carboxamide in the solvent, then adding the metal catalyst thereto, and conducting the reaction in the presence of hydrogen.

Suitable metal catalysts used in the reaction include Rh, Pt and Ru. When Ru is used, the reduction proceeds sterically selectively without causing racemization, and the decahydro(4aS, 8aS)isoquinoline-3(S)-carboxamide derivative (4) can be formed at good efficiency. Suitable Ru catalysts include Ru/C and Ru/alumina.

As the solvent used in the reaction, a solvent which is free from an aromatic ring and which is unreactive with a substrate can be used. Such a solvent includes alcohols (methanol, ethanol, 2-propanol, butanol), esters (ethyl acetate, isopropyl acetate), acetic acid and water. Methanol, ethanol and 2-propanol are preferred with respect to a vapor pressure in the reaction and the treatment after the reaction. The hydrogen pressure is typically between 5 and 200 atm, preferably between 10 and 50 atm due to economics and reactivity. The reaction temperature is typically between 20 and 200° C., preferably between 80 and 120° C. to achieve maximal optical purity.

After completion of the reaction, the catalyst is separated (for example by filtration) and the residue is concentrated. The concentrate can easily be purified by crystallization using an appropriate solvent, for example, a hydrocarbon solvent such as hexane or heptane.

Alternatively, the concentrate can be crystallized as a salt with hydrochloric acid, an organic acid or the like. The thus-obtained crystal does not contain a stereoisomer and can easily be isolated and purified.

Having generally described this invention, a further understanding can be obtained by reference to certain specific examples which are provided herein for purposes of illustration only and are not intended to be limiting unless otherwise specified.

EXAMPLES

Synthesis Example 1

One gram (5.64 mmols) of tetrahydroisoquinoline-3(S)-carboxylic acid (made by Aldrich) and a solution of 0.67 g (2.26 mmols) of triphosgene in 10 ml of tetrahydrofuran were heat-stirred at 60° C. for 3 hours. After the completion of the reaction, the solvent was distilled off, and the residue was dissolved in 5 ml of tetrahydrofuran and 10 ml of dichloromethane. The resulting slurry was added dropwise to a solution of 2.97 ml (28.2 mmols) of tert-butylamine in 10 ml of tetrahydrofuran. The mixture was stirred overnight at room temperature. The reaction mixture was acidified with 30 ml of 1-N hydrochloric acid, and was separated. Further, the organic layer was reversely extracted into the aqueous layer three times with 10 ml of 1-N hydrochloric acid. The aqueous layer was all collected, alkalified with 20 ml of a 4-N sodium hydroxide solution, and extracted twice with 20 ml of dichloromethane. The organic layer was dried over anhydrous sodium sulfate, and the solvent was then distilled off to obtain 1.11 g of a pale yellow solid in a yield 84.7%.

One gram of the above-obtained pale yellow solid was heat-recrystallized from 8 ml of hexane to obtain 0.918 g of N-tert-butyltetrahydroisoquinolinecarboxamide as a white crystal in a yield of 91.8%.

Optical rotation: $[\alpha]^D{}_{20}$=−111.57 (c=1.0, MeOH)
$^1$HNMR(CDCl$_3$): 7.2-7.1, 7.1-7.0(m,5H,arom and NHCO), 3.99(s,2H,NH—C$\underline{H}_2$-arom), 3.43(dd,1H,J=10.7Hz,5.1Hz, NH—C$\underline{H}$—CO), 3.21(dd,1H,J=16.5Hz,4.9Hz,CH—C$\underline{H}_2$-arom), 2.79(dd,1H, J=16.5Hz,10.7Hz,CH—C$\underline{H}_2$-arom), 1.65(s,1H,N$\underline{H}$—CH2-arom), 1.37(s,9H,t-Bu), 13CNMR (CDC13): 172.2, 135.8, 134.5, 129.3, 126.5, 126.1, 125.5, 57.1, 50.6, 47.8, 31.1, 28.7.

Synthesis Example 2

Two grams (11.3 mmols) of tetrahydroisoquinolinecarboxylic acid and a solution of 1.33 g (4.48 mmols) triphosgene in 20 ml of tetrahydrofuran were heat-stirred at 60° C. for 3 hours. The reaction solution was hot-filtered, and the filtrate was cooled to 0° C. for 4 hours to obtain 781 mg of a pale yellow NCA crystal in a yield of 34.1%.

IR : 1635, 1459, 1403, 1318, 744 cm$^{-1}$ $^1$HNMR(DMSO-d$_6$): 7.3-7.2(m,4H,arom), 4.78(d,1H,J=16.7Hz,arom-C$\underline{H}$—N), 4.46(d,1H,J=16.7Hz,arom-C$\underline{H}$2—N), 4.62(dd,1H, J=5.6Hz,10.8Hz,CH—N), 3.3-3.1(m,2H,CO—CH—C$\underline{H}_2$) $^{13}$CNMR (DMSO-d$_6$): 169.8, 150.7(N—CO—O), 131.2, 130.4, 129.4, 127.0, 126.9, 126.7, 54.3, 41.9, 28.9

Synthesis Example 3

Two grams (8.61 mmols) of N-tertbutyltetrahydroisoquinolinecarboxamide and a solution of 0.20 g (98.4 mmols) of 5% Ru/C in 20 ml of 2-propanol were stirred in an autoclave for 20 hours first at room temperature and a hydrogen pressure of 30 atm and then at 100° C. Subsequently, the reaction mixture was cooled, and the catalyst was separated by filtration. The filtrate was distilled off under reduced pressure, and the residue was crystallized from hexane to obtain 1.07 g of N-tertbutyldecahydro(4aS, 8aS)isoquinoline-3(S)-carboxamide as a primary (crystal in a yield of 52.1% and 0.42 g of as a secondary crystal in a yield of 20.7%.

Melting point: 116–117° C.

Optical rotation: $[\alpha]^D{}_{20}$ =−72.7 (c=0.5, methanol)
$^1$HNMR(CDCl$_3$): 6.54(bs,1H,CO—N$\underline{H}$), 3.1-3.0(m,1H,C$\underline{H}$—NH), 2.9-2.7(m,2H,C$\underline{H}_2$—NH), 1.9-1.2(13H, cyclohexane-ring,CO—CH—C$\underline{H}_2$, and CH—NH), 1.37(s, 9H,t-Bu)
$^{13}$CNMR(CDCl$_3$): 173.5(CO), 61.7, 51.7, 50.4, 35.5, 34.4, 31.7, 29.6, 28.8, 26.4, 24.9, 20.7

Synthesis Example 4

Phosgene gas (1.17 kg) was induced into the mixture of dichloromethane (9.8 L) and tetrahydrofuran (1.7 L) at −5° C. To this solution, tetrahydroisoquinoline-3(S)-carboxylic acid (1.05 kg) in dichloromethane (4.SL) and tetrahydrofurane (0.8 L) was added. After the reaction mixture was stirred at 45° C. for 20 hours, the solvent was distilled to dryness. To the residue, dichloromethane (17.8 L) was added and the solvent was distilled off again. The resulting slurry, which was cooled to 0° C., was added to a solution of 1.30 kg of tert-butylamine in 6.1 L of dichloromethane at under 5° C. for 1 hour. After 1 hour, 14.0 L of water was added, and the organic layer was separated. The organic layer was washed with 3.5 L of water and was reversely extracted two times with 7.0 L of 1-N hydrochloric acid. The aqueous layer was treated with active carbon at 75° C. and was filtered. The filtrate was neutralized with 1.4 L of 29% sodium hydroxide solution. After cooling at 0° C., the precipitated crystals were separated and dried to give 1.00 kg of N-tertbutyltetrahydroisoquinolinecarboxamide as a white crystal in a yield of 72.5%.

Synthesis Example 5

Ten grams of tetrahydroisoquinoline-3(S)-carboxylic acid and 7.4 gram of triphosgen in 100 ml of tetrahydrofuran was stirred for 5 hours at 55° C., for 4 hours at 60° C. and for 1 hour at 65° C. Fifty ml of solvent was distilled off and fifty ml of heptane was added. The precipitated crystals were filtered and washed with 10 ml of heptane. After dryness under reduced pressure overnight to give 9.34 gram of NCA in a yield of 81.5%.

Synthesis Example 6

To a solution five gram of N-tertbutyltetrahydroisoquinolinecarboxamide and 0.50 gram of 5% Ru/C in 33 ml of 2-propanol in an autoclave, 30 atm of hydrogen gas was introduced at room temperature. After stirred for 16 hours at 100° C., the reaction mixture was cooled to room temperature and the catalyst was separated. To the reaction mixture, 15 ml of heptane was added. After cooling at 0° C., the crystals were precipitated. The precipitates were filtered and dried to give 3.14 gram of white crystals N-tertbutyldecahydro (4aS, 8aS)isoguinoline-3(S)-carboxamide in 61.2% yield.

The present application is based on Japanese Patent Application No. 166536/1995 filed on Jun. 30, 1995; incorporated herein by reference.

Having now fully described the invention, it will be apparent to one of ordinary skill in the art that many changes

What is claimed as new and desired to be secured by Letters: Patent of the United States is:
1. Optically active tetrahydroisoquinoline-3(S)-carboxylic acid N-carboxy anhydride of the formula (2)
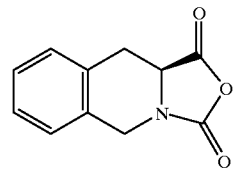
(2)